US00RE42050E

(19) United States
(12) Reissued Patent
Richard

(10) Patent Number: US RE42,050 E
(45) Date of Reissued Patent: Jan. 18, 2011

(54) LAPAROSCOPIC SPECIMEN REMOVAL APPARATUS

(76) Inventor: Marlon S. Richard, 118 Blackfin Cove, Slidell, LA (US) 70458

(21) Appl. No.: 10/841,427

(22) Filed: May 7, 2004

Related U.S. Patent Documents

Reissue of:
(64) Patent No.: 6,383,195
Issued: May 7, 2002
Appl. No.: 09/288,686
Filed: Apr. 9, 1999

U.S. Applications:
(60) Provisional application No. 60/081,609, filed on Apr. 13, 1998.

(51) Int. Cl.
*A61B 17/24* (2006.01)

(52) U.S. Cl. ..... 606/114
(58) Field of Classification Search ..... 606/114, 606/110, 106, 127, 113, 101, 121
See application file for complete search history.

(56) References Cited

U.S. PATENT DOCUMENTS 4,467,802 A * 8/1984 Maslanka ..... 606/206
4,611,594 A 9/1986 Grayhack et al.
5,176,687 A 1/1993 Hasson et al.
5,190,561 A * 3/1993 Graber ..... 606/127
5,279,548 A * 1/1994 Essig et al. ..... 604/27
5,312,417 A 5/1994 Wilk
5,370,647 A 12/1994 Graber et al.
5,486,183 A 1/1996 Middleman et al.
5,643,282 A * 7/1997 Kieturakis ..... 606/114
5,908,435 A 6/1999 Samuels
5,924,175 A * 7/1999 Lippitt et al. ..... 24/537
6,001,118 A * 12/1999 Daniel et al. ..... 606/200

* cited by examiner

*Primary Examiner*—Pedro Philogene
(74) *Attorney, Agent, or Firm*—Garvey, Smith, Nehrbass & North, L.L.C.; Brett A. North

(57) ABSTRACT

An improved retractable cleat device having a housing and a telescopic cleat member absent a handle. The telescopic cleat member is lockable in the housing in a retracted position via a cam channel having at least one interval engaging a cam follower. The cam channel includes at least one interval which unlocks the telescopic cleat and allows the telescopic cleat to move to an upraised position via a bias force of a compression spring.

33 Claims, 8 Drawing Sheets

LAPAROSCOPIC SPECIMEN REMOVAL APPARATUS

Matter enclosed in heavy brackets [ ] appears in the original patent but forms no part of this reissue specification; matter printed in italics indicates the additions made by reissue.

This application claims the benefit of priority of U.S. Provisional Application Serial No. 60/081,609 filed Apr. 13, 1998.

BACKGROUND OF THE INVENTION

1. Field of the Invention

The present invention relates to laparoscopic instruments and, more particularly, to laparoscopic specimen removal apparatuses.

2. General Background

One of the biggest concerns in laparoscopic surgery is the number of laparoscopic instruments required to perform the surgical procedure and thus the number of incisions in the patient to insert such instruments. Therefore, several attempts have been made to integrate the functions of different laparoscopic instruments in such a manner that the number of incisions or trocar sites required to carry out the surgical procedure is minimized. However, any such integration of functions should not complicate the overall surgical procedure but instead simplify.

Before extracting the tissue or specimen from the patient's cavity, the tissue/specimen is placed in a receptacle such as, a bag, web or sheath to minimize further exposure of the other organs from the possibly diseased tissue/specimen being removed. As can be surmised, the bag or receptacle must be opened and/or deployed and, preferably, closed while in the patient cavity.

Several laparoscopic instruments have been patented which are used to assist in tissue removal during laparoscopic surgery.

U.S. Pat. No. 5,630,822, issued to Hermann et al., discloses a laparoscopic tissue removal device which includes a grasper coaxially mounted within an expandable sheath and including jaws for grabbing a specimen. However, a second tool must be used to tie off the sheath. Additionally, the use of other conventional laparoscopic grasping tools to push the mass into the flared end of the sheath is disclosed.

U.S. Pat. Nos. 5,190,555, issued to Wetter et al.; 5,336,227, issued to Nakao et al.; and, 5,352,184, issued to Goldberg et al. all disclose laparoscopic tools with a bag for capturing tissue, closing the bag via a drawstring and withdrawing it back through the tool.

U.S. Pat. Nos. 5,496,330, issued to Bates; 5,658,296, issued to Bates et al.; and, 5,197,968, issued to Clement all disclose a laparoscopic tools where the tool has a flexible basket for the tissue capture.

U.S. Pat. Nos. 5,176,687, issued to Hasson et al. and 5,312,417, issued to Wilk disclose laparoscopic tools with an open ended bag to capture tissue samples. In the Hasson et al. patent ('687), though a laparoscopic removal tool can be inserted through the bag, the bag must be pulled down out of a sleeve and opened with the assistance of a second tool, such as, forceps. The bag in '687 is made of a membrane which is not rigid and has no rigid supports to allow it to open on its own inside a patient. In the Wilk patent ('417), the receiver portion or open ended web (bag) is provided with support means to open and expand the open ended web (bag). Numerous proposals are suggested to open the receiver portion or web including complicated techniques using hydraulic or pneumatic circuits. Nevertheless, the invention described in '417 does not disclose any means in the laparoscopic cannula assembly which serves to close the open end of the web (bag) and, more specifically, the support means supporting the web (bag).

U.S. Pat. Nos. 5,190,1555, 5,336,227, 5,352,184, 5,496,330, 5,312,417, 5,197,968, 5,176,687; 5,630,822, 5,658,296, 5,423,830 are incorporated herein by reference.

U.S. Pat. Nos. 5,465,731 and 5,647,372, both of which are assigned to United States Surgical Corporation, disclose a specimen removal pouch and applicator which includes a pouch closed via a drawstring. An additional forceps or grasper inserted though another cannula may be need to unroll the pouch if necessary. The disclosed specimen removal pouch and applicator is not adapted to have a laparoscopic grasper or other laparoscopic instrument inserted coaxially through the applicator.

U.S. Pat. No. 5,480,404, issued to Kammerer et al., discloses a surgical tissue retrieval instrument including a collapsible pouch having a cinching mechanism. The instrument of Kammerer et al., like the applicator disclosed in '731 and '372, is not adapted to have a laparoscopic grasper or other laparoscopic instrument inserted coaxially therethrough.

U.S. Pat. No. 5,423,830, issued to Schneebaum et al., discloses an instrument assembly having a capture component including a web member attached to spring biased ribs which opens into a cup-shaped configuration when ejected. A vacuum or suction source is provided to provided a negative pressure to assist in clamping the web member and ribs around the tissue/specimen. The instrument assembly of Schneebaum is not adapted to have the cauterization loop inserted coaxially through the web.

U.S. Pat. No. 5,074,867, issued to Wilk, discloses a membrane or web having stings or filaments attached to the periphery or corners thereof. Forceps or the like are used to stretch the membrane until it assumes a substantially opened position which is shown as a flat sheet-like profile. The strings are used to surround the membrane or web around the specimen or organ.

As can be readily seen, there is a continuing need for a laparoscopic specimen removal apparatus including a laparoscopic specimen extractor having a specimen bag having support means for allowing the bag to be opened and closed without the use of a separate laparoscopic tool; and, a specimen grasper coaxially mountable within the specimen bag.

SUMMARY OF THE PRESENT INVENTION

The preferred embodiment of the laparoscopic specimen removal apparatus of the present invention solves the aforementioned problems in a straight forward and simple manner. What is provided is an apparatus for removing specimens from a patient during laparoscopic surgery comprising a laparoscopic specimen extractor having a specimen bag having support means for allowing the bag to be opened and closed without the use of a separate laparoscopic tool; and, a specimen grasper coaxially mountable within the specimen bag.

Broadly, the laparoscopic specimen extractor comprises:

(a) a bag having open ends;

(b) a means for supporting said bag having a plurality of tips' wherein said support means is spring biased and uniquely arranged to automatically open into a tulip shape when ejected to a deployed position;

(c) means coupled to said plurality of tips for cinching closed said support means; and (d) a pathway, formed coaxially through said laparoscopic specimen extractor and said support means and having said cinching closed means journalled axially therethrough wherein said pathway is adapted to have inserted coaxially therethrough a grasping laparoscopic instrument for retrieving said specimen, adapted to have retracted therethrough said grasping laparoscopic instrument to deposit said specimen in said bag and adapted to aspirate or morcelate said specimen in said bag therethrough.

The support means cinches closed to a generally elliptical or football shape.

In view of the above, it is an object of the present invention to provide a laparoscopic specimen removal apparatus which includes a laparoscopic specimen extractor having a cage lined with a liner or bag which automatically expands and opens to a "tulip" shape when deployed and means secured to the cage for cinching closed distal ends or tips of the cage when opened.

Another object of the invention is to provide such a cage or support means with a plurality of spring biased strips having tips wherein a first set of the strip tips are tied together via a first drawstring and a second set of the strip tips are tied togther via a second drawstring. Pulling the first and second drawstrings cinches closed the tips and, thus, the liner or bag attached to the cage.

A further object of the present invention is to provide such a cage or support means which when closed the plurality strips are essentially straight, when opened forms a "tulip" shape and when cinched closed forms an "elliptical" or "football" shape.

A further object of the present invention is to provide a support means which include rigid but flexible strips which are secured to the bag.

It is a still further object of the present invention to provide such a laparoscopic specimen extractor with a cinching closed means including first and second drawstrings and a means for pulling the drawstrings simultaneously to cinch close the cage or support means.

It is a still further object of the present invention to provide the cage or support means with a plurality of strips wherein each strip has a free end twisted approximately 90° (ninety degrees) with respect to the rest of the strip to form a twisted section and a hole is bored in such twisted section. This twisted section is substantially perpendicular to the center axis of inner tube assembly and thus the cage. Likewise, the center of the holes in the twisted sections is substantially perpendicular to said center axis. Thereby, as the tips (twisted section) is cinched closed via the drawstring the twisted section are drawing toward each other so that an "elliptical" or "football" shape is created.

In view of the above objects, it is a feature of the present invention to provide a laparoscopic specimen extractor which is simple to use and further does not complicate the tissue surgical procedure but instead simplifies it.

Another feature of the present invention is to provide a laparoscopic specimen extractor which is relatively simple structurally and thus simple to manufacture.

A major advantage of the laparoscopic specimen extractor it its utilization of a unique specimen entrapment system which compresses and forms the specimen into a "dilator" or "football" shaped package in which its cross section's diameter is much smaller than its length. This aerodynamic shape has the advantage of exiting a smaller incision with significantly less effort than conventional bag type retrieval systems which form the specimen into a "spherical" or basketball" shape which is difficult to pull through a small incision.

Another advantage of the present invention is the ability of the laparoscopic specimen extractor, through a single site, to (1) insert a grasping laparoscopic instrument through (coaxially) the extractors' center; (2) retrieve a specimen and pull the specimen into the specimen cage/bag assembly via the coaxially inserted grasping laparoscopic instrument; (3) compress the specimen cage/bag assembly into an aerodynamic package; (4) aspirate and/or morcelate the specimen in a protective environment; and, (5) remove the specimen from the patient's cavity.

The above and other objects, features and advantages of the present invention will become apparent from the drawings, the description given herein, and the appended claims.

BRIEF DESCRIPTION OF THE DRAWING

For a further understanding of the nature and objects of the present invention, reference should be had to the following description taken in conjunction with the accompanying drawings in which like parts are given like reference numerals and, wherein.

DETAILED DESCRIPTION OF THE PREFERRED EMBODIMENT

Figure 2:
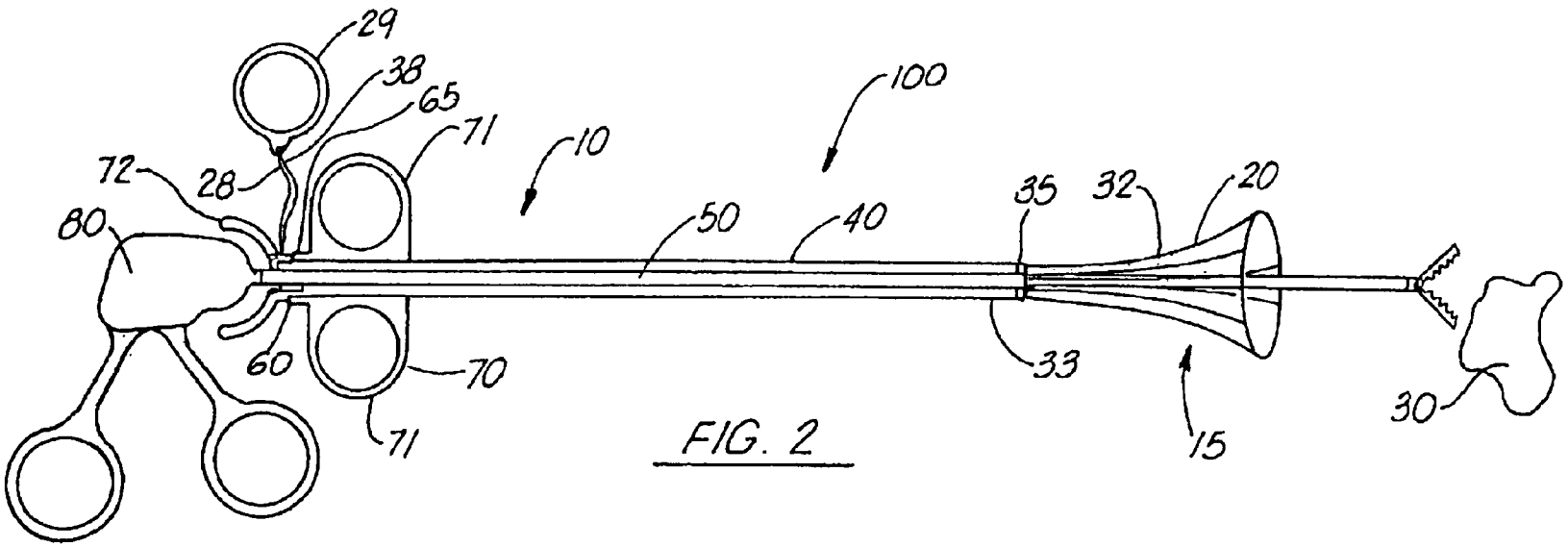
FIG. 2 illustrates a cross-sectional view of the laparoscopic specimen removal apparatus of the present invention with the cage/bag assembly in the open deployed position.
Figure 3:
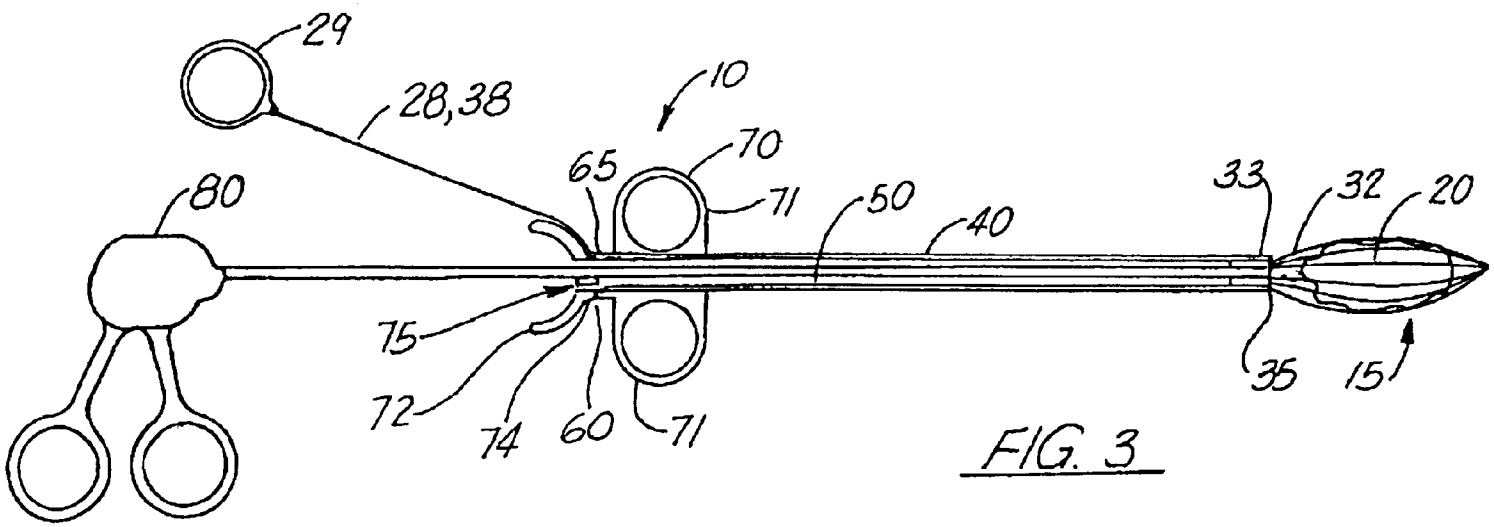
FIG. 3 illustrates a cross-sectional view of the laparoscopic specimen removal apparatus of the present invention with the cage/bag assembly in the closed position.

FIGS. 2 and 3 illustrates a cross-sectional view of the laparoscopic specimen removal apparatus 100 of the present invention with the cage/bag assembly 15 in the open deployed position. The laparoscopic specimen removal apparatus 100 includes in general laparoscopic specimen extractor 10 and grasping laparoscopic instrument 80.

Figure 1:
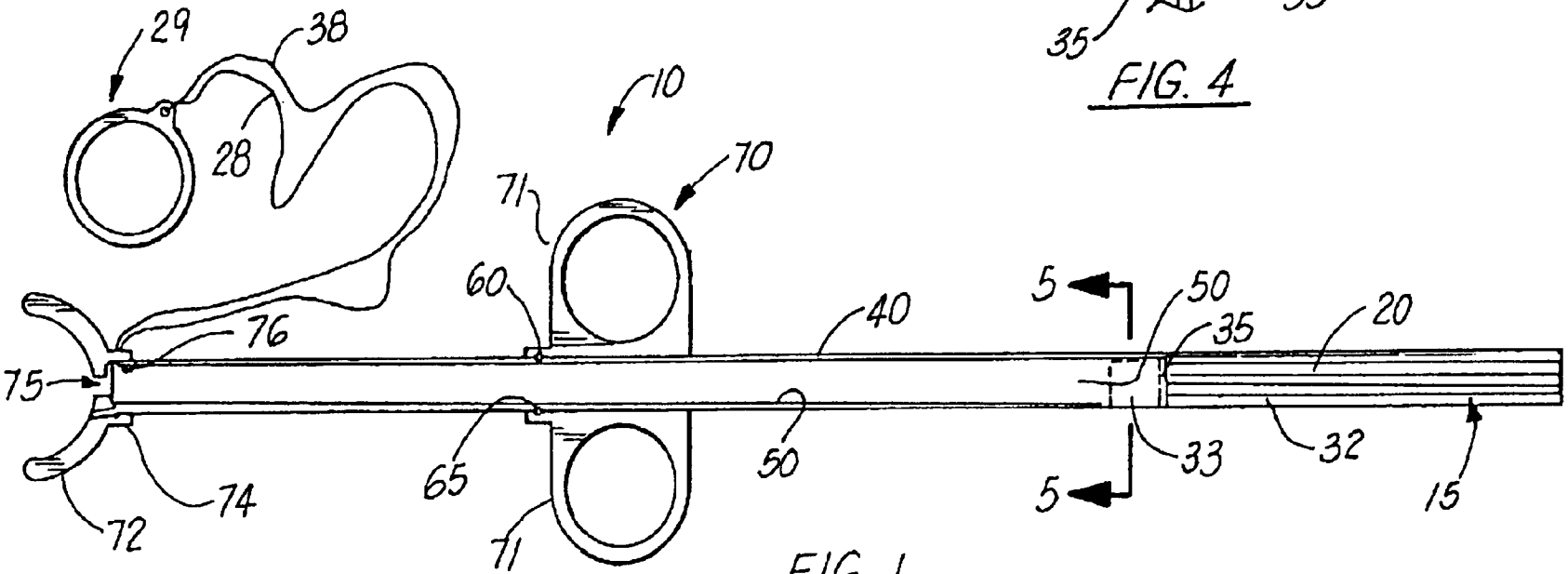
FIG. 1 illustrates a cross-sectional view of the laparoscopic specimen extractor of the present invention with the cage/bag assembly in the retracted position.

FIG. 1 is a cross-sectional view showing the laparoscopic specimen extractor 10 with the specimen cage/bag assembly 15 in a retracted position. The laparoscopic specimen extractor apparatus 10 is a laparoscopic device used to facilitate the removal of a specimen 30 from a patient's cavity through a trocar or trocar site. The laparoscopic specimen extractor 10 basically has a tube inside a tube design.

The laparoscopic specimen extractor 10 in general comprises a specimen cage/bag assembly 15, an outer tube assembly 40, serving as the container for the specimen cage/bag assembly 15, and an inner tube assembly 50 which is slidably coupled in the outer tube assembly 40 and has the specimen cage/bag assembly 15 on its patient end.

The outer tube assembly 40 is fabricated of surgical-grade stainless steel or any other biocompatible material having a diameter of 10 mm with a wall thickness of approximately 0.25 mm. A collar 60, made of the same material as the outer tube assembly 40, is 13 mm in diameter and 10 mm long with a wall thickness of approximately 1.5 mm. The collar 60 is axially fused to the operator end of the outer tube assembly 40. The collar 60 has a groove approximately 1 mm wide cut into the inner circumference, positioned 1.5 mm from the open end of the collar 60. Such groove accommodates a 9.5 mm surgical grade O-ring 65 which provides an air-tight seal with the inner tube assembly 50.

A finger ring assembly 70, made of surgical-grade stainless steel, or any other biocompatible material, is mounted at the collar end or, in other words, the operator end, of the outer tube assembly 40, surrounding the collar 60. The finger ring assembly 70 contains two (2) rings 71 oriented across from each other, resembling finger holes of a large syringe. The rings 71 have approximately a 15 mm inner diameter and a 3 mm ring thickness or width and are positioned approximately 20 mm from the collar end of the tube assembly 40 to the ring's centers. The total length of the outer tube assembly 40 is approximately 200 mm.

The inner tube assembly 50 is fabricated of surgical grade stainless seel or any other biocompatible material. The inner tube assembly 50 has an outer diameter of 9.5 mm with a wall thickness of approximately 0.25 mm and a length of 200 mm. The inner tube assembly 50 has external threads (not shown), on the operator end, 8 mm long with an outer diameter of approximately 11 mm. An internally threaded end cap 74, which has an integrated thumb cradle 72, is threaded onto the operator end of the inner tube assembly 50.

Referring also to FIGS. 2 and 3, a 6 mm hole 75 is bored through the center of the end cap 74, as best seen in FIG. 1, to accommodate the grasping laparoscopic instrument 80. The grasping laparoscopic instrument 80 is to be coaxially inserted through the center of thumb cradle 72 down through the inner tube assembly 50. Two (2) small holes 76, approximately 0.5 mm, are bored into the side of the end cap 74 to allow a passage for two (2) drawstrings 28 and 38 which are tied to ring 29. A seal (not shown) fabricated of surgical grade silicone or any other medical grade flexible material which has a diameter of 10 mm and a thickness of 0.20 mm with a 5 mm flexible hole in the center aligned with the hole 75 in the end cap 74 is installed between the operator end and the underside surface of the end cap 74. This seal prevents gas from leaking around the laparoscopic instrument 80 when inserted. A plug (not shown), which is 10 mm long having an outer diameter of 6 mm fabricated of medical grade silicone, is used to plug the hole 75 in the end cap 74 and, when not in use, is tethered from the end cap 74. This plug prevents gas from leaking from the patient to atmosphere before insertion of extractor 10.

Figure 6:
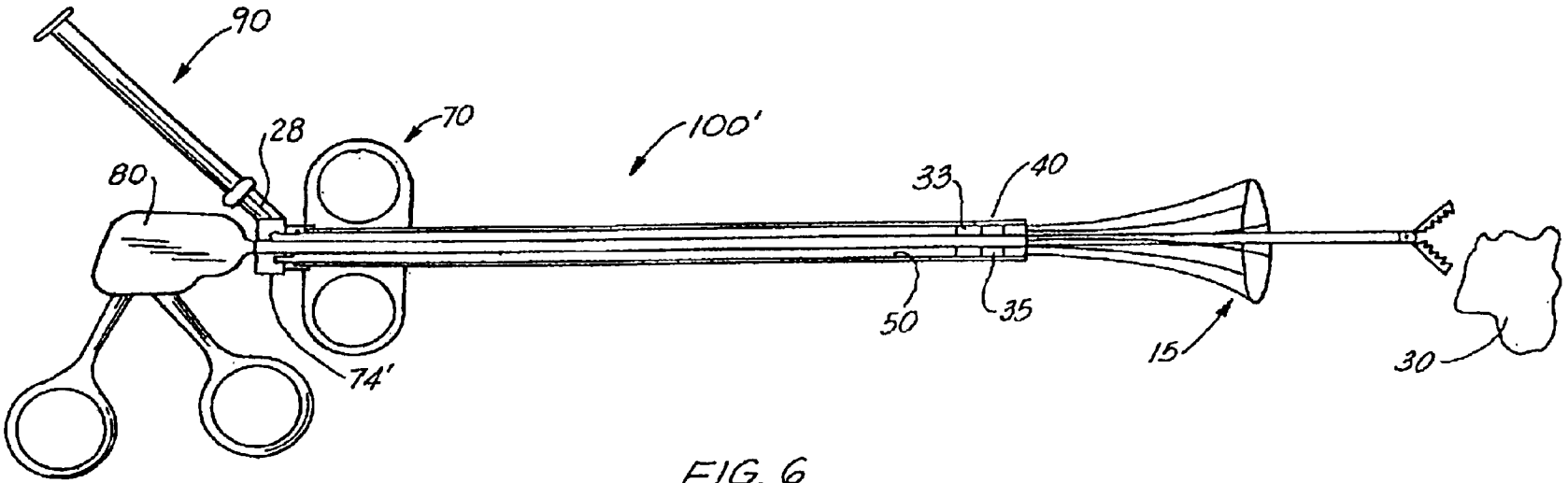
FIG. 6 illustrate a first alternate embodiment of the laparoscopic specimen removal apparatus of the present invention with the cage/bag assembly in the open deployed position.
Figure 7:
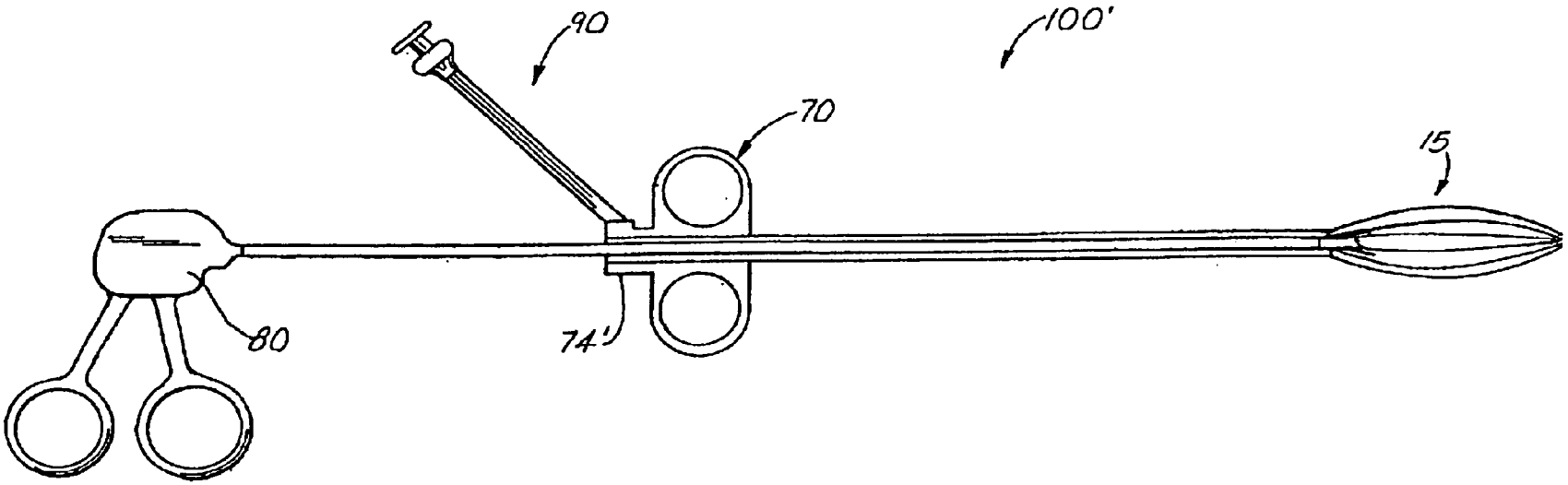
FIG. 7 illustrates the first alternate embodiment of the laparoscopic specimen removal apparatus of the present invention with the cage/bag assembly in the closed position.

Referring now to FIGS. 6 and 7, an alternate embodiment of the laparoscopic specimen removal apparatus 100' is shown. The primary difference is that in lieu of ring 29 and integrating the thumb cradle 72 with end cap 74, a drawstring handle assembly 90 is substituted. The drawstring handle assembly 90 includes internally threaded end cap 74' which is threaded onto the operator end of inner tube assembly 50 and a rod or handle 91 which is integrated with the end cap 74' to radially project from the outer circumferential surface of end cap 74' at approximately 45° (forty-five degrees). The draw drawstring handle assembly 90 further includes a palm rest 92 affixed to the free end of the rod or handle 91 and a sliding finger squeeze slide 93.

Like end cap 74, end cap 74' is provided with a bored hole 75', for the insertion of the laparoscopic instrument 80 and the bored side holes 76' (only one shown) for the passage of the two (2) drawstrings 28 and 38. The free ends of the draw strings 28 and 38 are affixed or tied to the sliding finger squeeze slide 93 slidably mounted on rod or handle 91. In the exemplary embodiment, when the operator squeezes the fingers on finger squeeze slide 93, sliding finger squeeze slide 93 slides upward toward palm rest 92 thereby simultaneously pulling drawstrings 28 and 38 to cinch close cage 20.

Figure 9:
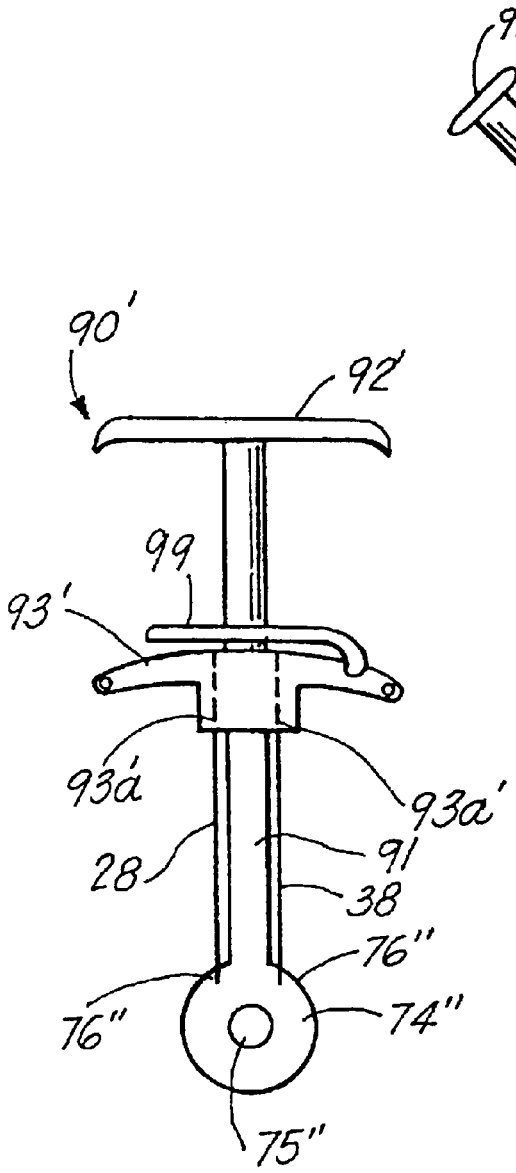
FIG. 9 illustrates an alternate embodiment of the drawstring handle assembly.
Figure 8:
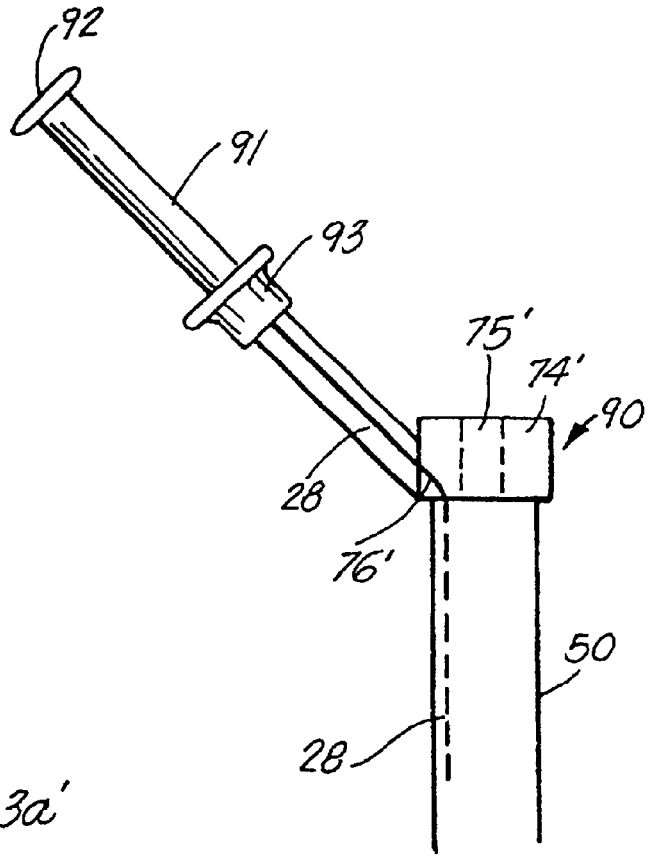
FIG. 8 illustrates a top view of the drawstring handle assembly of FIG. 6.

Referring now to FIG. 9, in lieu of the drawstring handle assembly 90, drawstring hand assembly 90' is substituted. The drawstring handle assembly 90' includes internally threaded end cap 74" which is threaded onto the operator end of inner tube assembly 50 and a rod or handle 91' which is integrated with the end cap 74' to radially project from the outer circumferential surface of end cap 74'. The draw drawstring handle assembly 90' further includes a palm rest 92' affixed to the free end of the rod or handle 91' and a sliding finger squeeze slide 93'. In this embodiment, palm rest 92' and squeeze slide 93' have an enlarged surface area. Locking means 99 holds slide 93' in the "up" position of FIG. 12, by frictional engagement (it binds itself) and attachment to slide 93' and can be released by movement toward slide 93'.

Like end cap 74', end cap 74" is provided with a bored hole 75", for the insertion of the laparoscopic instrument 80 and the bored side holes 76" for the passage of the two (2) drawstrings 28 and 38. The free ends of the draw strings 28 and 38 are affixed or tied to the sliding finger squeeze slide 93' slidably mounted on rod or handle 91' via holes 93a' and 93b'. Longitudinal bore holes 93a' and 93b' are position in close proximity to the outer perimeter edge of squeeze slide 93' so the operator's fingers can be positioned on the underside of squeeze slide 93' between the drawstrings 28 and 38 and rod or handle 91'.

Figure 10:
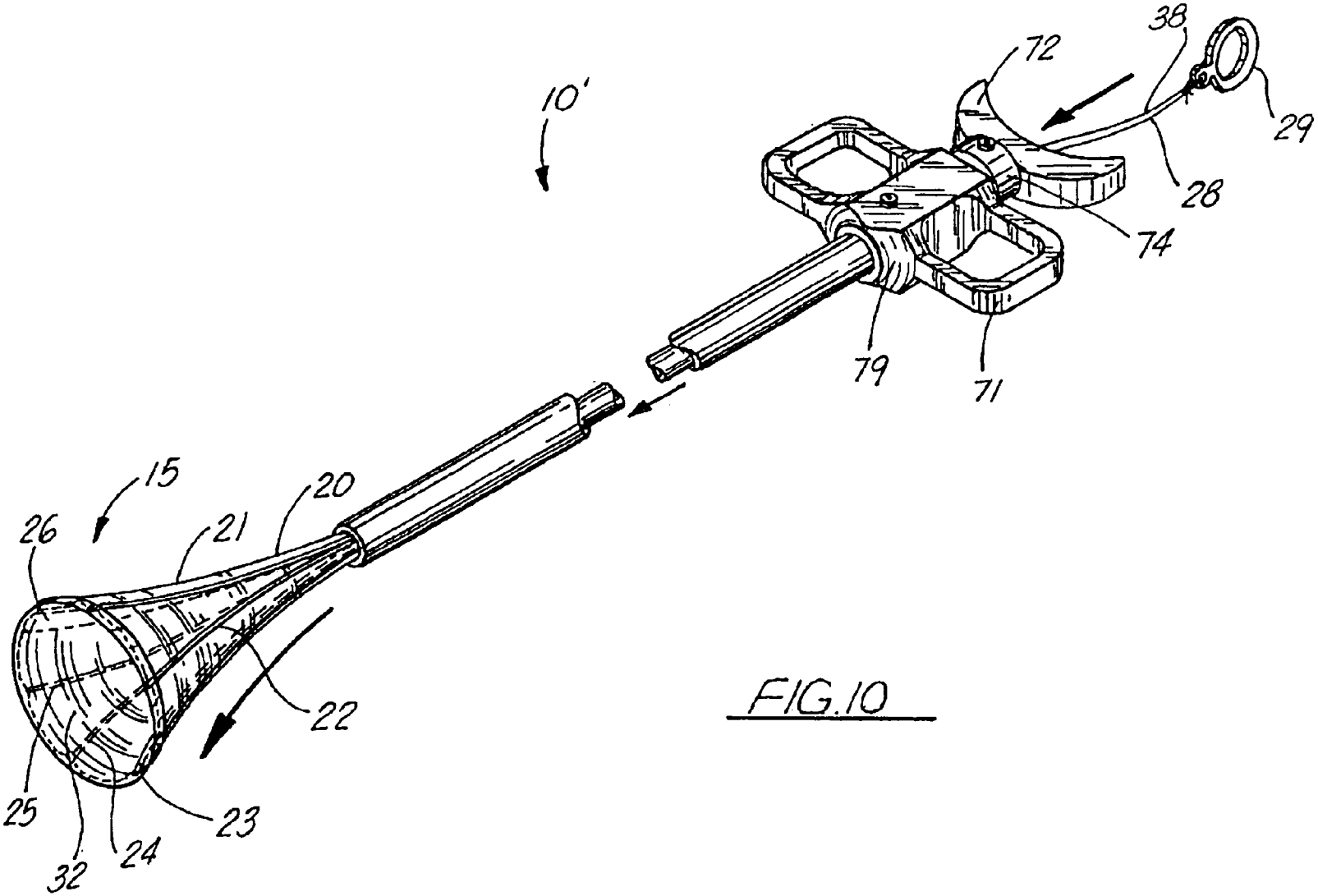
FIG. 10 illustrates a perspective view of a second alternate embodiment of the laparoscopic specimen extractor of the present invention with the cage/bag assembly in the deployed position.

Referring now to FIG. 10, a perspective view of an alternate embodiment of the laparoscopic specimen extractor 10' is shown. The primary difference between the laparoscopic specimen extractor 10' and the laparoscopic specimen extractor 10 of FIG. 1 is that the bored side holes 76 of FIG. 1 for the passage of the two (2) drawstrings 28 and 38 have been moved to a position adjacent the hole 75 formed in the end cap 74. Thereby, the drawstrings 28 and 38 exit the rear end of the end cap 74 and not through the side. Additionally, the finger rings 71' differ from the finger rings 71 in that finger rings 71' are squared in stead of circular.

The squared finger rings 71' are integrated with jacket 79 having a bored hole therethrough. The operator end of the outer tube assembly 40 has affixed thereto jacket 79 such that jacket 79 is stationary.

Figure 11:
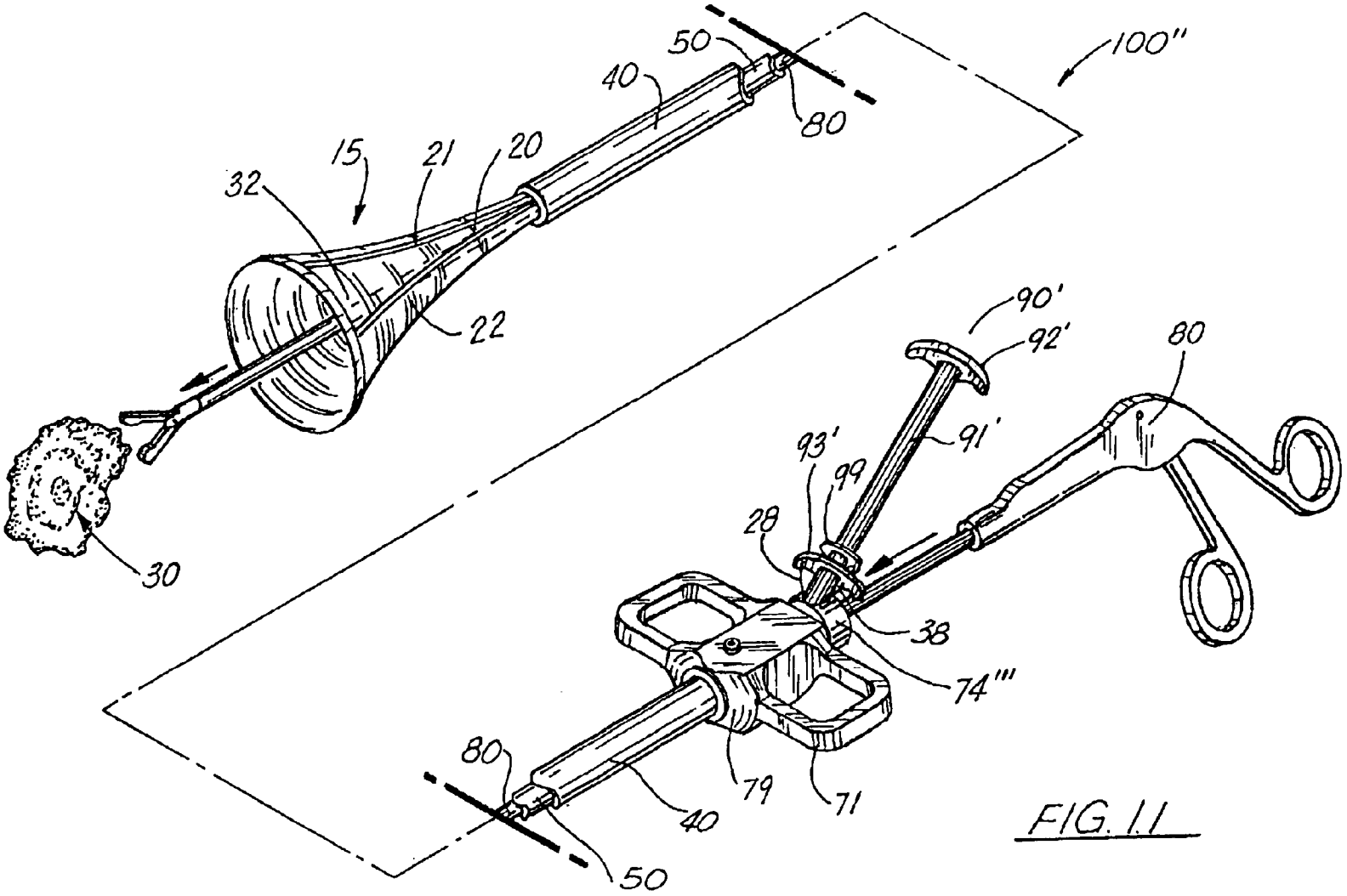
FIG. 11 illustrates an exploded perspective view of a fourth alternate embodiment of the laparoscopic specimen removal apparatus of the present invention with the cage/bag assembly in the deployed position.
Figures 12, 13:
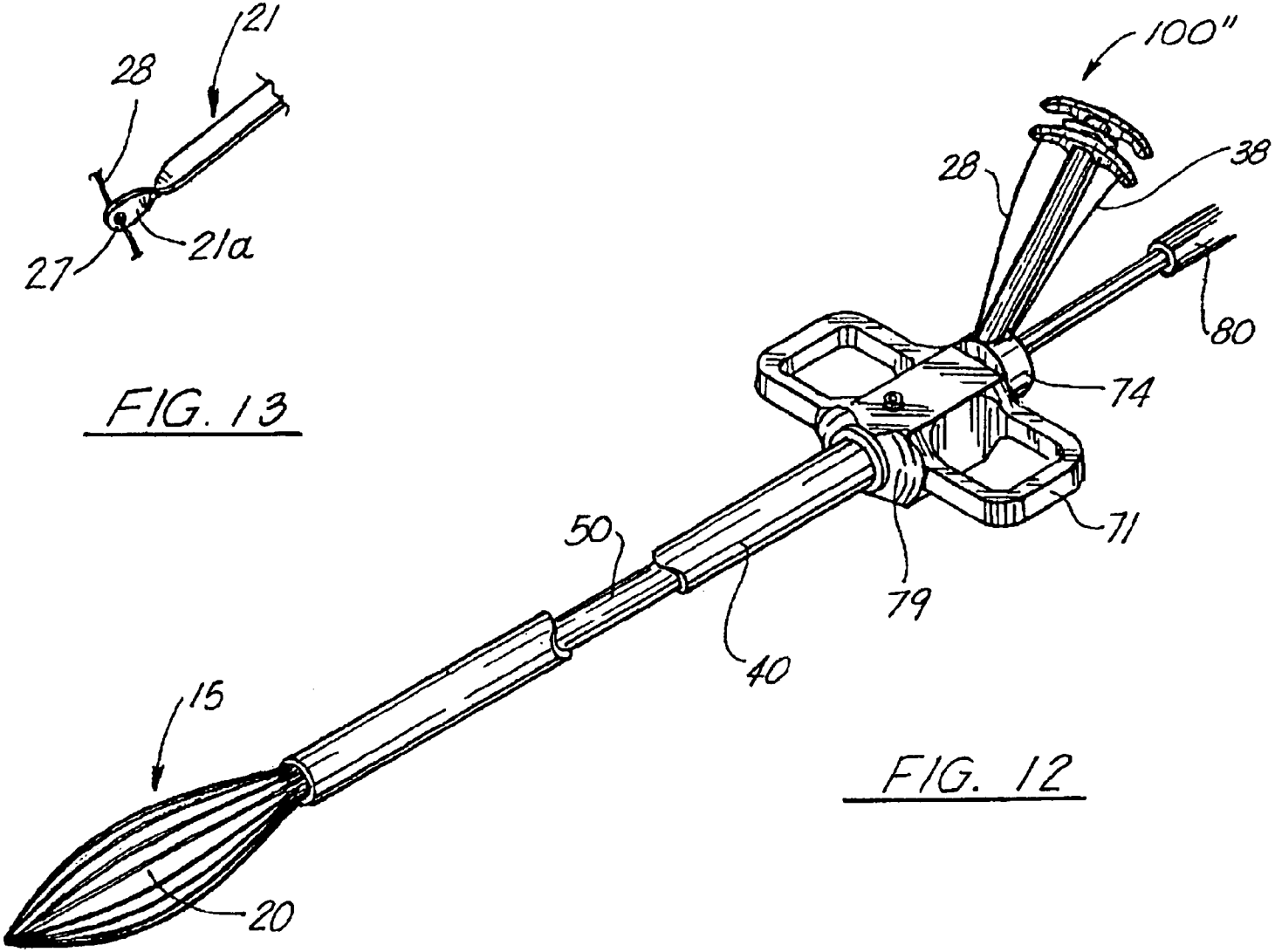
FIG. 12 illustrates a perspective view of a fifth alternate embodiment of the laparoscopic specimen removal apparatus of the present invention with the specimen cage/bag assembly closed in the substantially "elliptical" or "football" shape; and, FIG. 13 illustrates the twisted end section of a respective spring loaded strip.

Referring now to FIGS. 11 and 12, an alternate embodiment of the laparoscopic specimen removal apparatus 100" is shown. The primary difference is that in lieu of the thumb cradle 72 of FIG. 10, the drawstring handle assembly of FIG. 9 has been substituted. Furthermore, instead of affixing rod or handle 91' 90° (ninety degrees) with respect to the circumferential surface of end cap 74", rod or handle 91' is angled approximately 45° (forty-five degrees). FIG. 11 illustrates cage/bag assembly 15 of the laparoscopic specimen removal apparatus 100" deployed and in the open position. FIG. 12 illustrates cage/bag assembly 15 of the laparoscopic specimen removal apparatus 100" deployed and in the cinched closed position.

Figure 4:
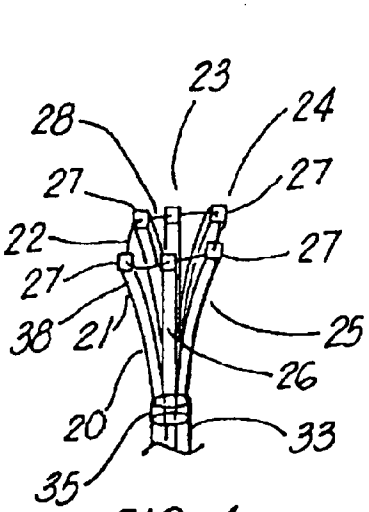
FIG. 4 illustrates a partial perspective view of the spring loaded strips in an open position.

Since the cage/bag assembly 15 of FIGS. 1–7 and 10–12 are essentially the same, the cage/bag assembly 15 shown in FIGS. 1–4 will be described herein in detail. At the patient end of inner tube assembly 50, six (6) spring loaded strips 21, 22, 23, 24, 25 and 26, fabricated of medical grad material approximately 120 mm long and 3 mm wide with a thickness of 0.40 mm, are mounted in a circular fashion spaced 60° (sixty degrees) apart to the inner circumference of the inner tube assembly 50. These spring loaded strips 21–26 are recessed approximately 15 mm inside of the inner tube assembly 50 and protrude out of the end of the inner tube assembly 50 approximately 105 mm. The protruding portion of the spring loaded strips 21–26 are curved outward approximately 20 mm from the tube's axis in an arc fashion, when in the retracted position, as best seen in FIGS. 2 and 4. The six (6) spring loaded strips 21–26 protruding from the inner tube assembly 50 are capable of forming a shape that resembles a "tulip", as best seen in FIGS. 2 and 4, when in a retracted position. This structure forms the specimen cage 20 or support means which supports the specimen liner or bag 32. Although six (6) strips 21–26 are shown, more or fewer strips could be used.

Since the spring loaded strips 21–26 protrude out of the end of the inner tube assembly 50 approximately 105 mm, the total length of the spring loaded strips 21–26 forming the cage 20 or support means ejected from the patient end of outer tube assembly 40 may be varied in accordance with the size of the specimen 30. Moreover, as the total length of the spring loaded strips is varied, the amount of expansion or flaring of these spring biased strips 21–26 is varied proportionally.

Referring also to FIG. 13, since each of the spring loaded strips 21–26 are essentially identical, only one such strip will be described in detail. On the unattached end, tip or free end of spring loaded strip 21, 7 mm of said unattached end is twisted at 90° (ninety degrees) with respect to the rest of the strip 21 thus forming a twisted end section 21a. A 0.5 mm hole 27 is bored in this twisted end section 21a 1.5 mm from the distal end thereof. The hole 27 accommodates one of two (2) drawstrings 28 and 38. This twisted section 21a is substantially perpendicular to the center axis of inner tube assembly 50 and thus the cage 20. Likewise, the center of the hole 27 in the twisted section 21a is substantially perpendicular to said center axis. Thereby, as the tips (twisted section 21a) is cinched closed via the drawstrings 28 and 38. The twisted sections of all the spring loaded strips 21–26 are drawn toward each other so that they are closely circumferentially stacked closely one after the other. Thereby, an "elliptical" or "football" shape is created. Moreover, holes 27 in each of the twisted sections provide a circumferential passageway for drawstrings 28 and 38 wherein the center of the circumferential passageway is perpendicular to the center axis of cage 20 and inner tube assembly 50.

Figure 5:
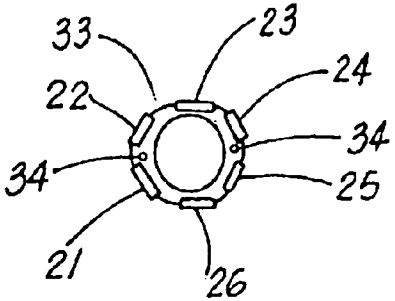
FIG. 5 illustrates a top view of the bag retaining collar.

Referring also to FIG. 5, the spring loaded strips 21–26 are held in place with an internal retaining collar 33 with an outer diameter of approximately 7.5 mm, a length of 15 mm and a 5 mm axially bored hole through the center to allow for the passage of laparoscopic instruments, such as, grasping laparoscopic instrument 80, therethrough. Also, two (2) holes 34 approximately 0.15 mm in diameter are bored to accommodate the two (2) drawstrings 28 and 38, respectively, therethrough. The collar 33 is fabricated from a medical grade stainless steel or any other biocompatible material and is positioned approximately 7 mm from the patient end of the inner tube assembly 50. The spring loaded strips are numbered in a clockwise manner 21, 22, 23, 24, 25 and 26 with 21 being adjacent 26.

The drawstring 28, which is 400 mm long and made of #0 silk suture or any biocompatible ligature, is tied with an appropriate knot through the hole 27 of strip 21; the other end is passed or threaded through the hole 27 in the strips 22, 23 and 24 making a 90° (ninety degree) turn running parallel along the top of strip 24, through one of the holes 34 in the retaining collar 33, through the center of the inner tube assembly 50, and exiting through one of the holes 76 or 76' in the end cap 74 or 74'. The end of drawstring 28 is tied off to a ring 29 or any approximate handle assembly 90 or 90', in the manner as described above. When the drawstring 28 is pulled, strips 21, 22, 23 and 24 will be drawn together. More specifically, the ends or tips of spring loaded strips 21–24 are drawn together.

A second drawstring 38, which is 400 mm long and, likewise, made of #0 silk suture or any biocompatible ligature, is tied with an appropriate knot through the hole 27 of strip 24; the other end is passed through the hole 27 in strips 25, 26 and 21 making a 90° (ninety degree) turn running parallel along the top of the strip 21, through the other one of holes 34 in the retaining collar 33, through the center of the inner tube assembly 50, exiting through the other one of holes 76 or 76' in the end cap 74 or 74'. The end of drawstring 38 is tied off to the same ring 29 or any appropriate handle assembly 90 or 90', as is the other drawstring 28. When the drawstring 38 is pulled, the strips 24, 25, 26 and 21 will be drawn togther. More specifically, the ends or tips of spring loaded strips 21 and 24–26 are drawn together.

When both drawstrings 28 and 38 are pulled simultaneously all the ends or tips of the six (6) spring loaded strips 21–26 will be drawn together, thus forming a substantially "elliptically" or "football" shaped cage 20 or support means, as best seen in FIG. 3, trapping the specimen 30 inside. As the ends or tips of the spring loaded strips 21–26 are drawn together the cage 20 or support means forms a "dilator" or "football" shaped package in which its cross section's diameter is much smaller than its length. This aerodynamic shape has the advantage of exiting a smaller incision with significantly less effort than conventional bag type retrieval systems which form the specimen into a "spherical" or "basketball" shape which is difficult to pull through a small incision.

A cylindrical liner or bag 32 made of surgical grade plastic, such as the material found in U.S. Surgical's Endo Catch, would be suitable for this application and is positioned inside the spring loaded strips 21–26 and hemmed around the drawstrings 28 and 38 and the strip ends or tips. The other end of the cylindrical liner or bag 32 is secured to the inner circumferential wall of the patient end of the inner tube assembly 50 and is held in place by a medical grade bag retaining ring 35. The bag retaining ring 35, having an opening of 6 mm, is positioned in front of the internal retaining collar 33. This liner or bag 32 prevents leakage of specimen fluids during extraction.

All of the above individual measurements and dimensions could be reduced by 99.999% or enlarged by 10,000% to fit a specific application.

The laparoscopic specimen extractor 10 is assembled by inserting the inner rube assembly 50 inside the outer tube assembly 40 through the operator end.

The inner tube assembly 50 has two (2) positions, retracted (FIG. 1) and deployed (FIG. 2). In the deployed position, preferably, the patient end of the inner tube assembly 50 is even with the patient end of the outer tube assembly 40, allowing the specimen cage/bag assembly 15 protruding from the patient end of inner tube assembly 50 to be exposed and opened, as best seen in FIG. 2. In the retracted position, the inner tube assembly 50 is pulled back approximately 105 mm, causing the cage 20 or support means and the liner 32 to collapse and be contained within outer tube assembly 40, as best seen in FIG. 1.

The operation of the laparoscopic specimen extraction 10 of the laparoscopic specimen removal apparatus 100 is described below. The laparoscopic specimen extractor 10 is inserted, patient-end first, into a trocar or open incision in the retracted position, as best seen in FIG. 1. The laparoscopic specimen extractor 10 is then deployed by inserting two (2) fingers in the finger rings 71 on the outer tube assembly 40 and placing the thumb in the thumb cradle 72 on the end cap 74. The operator slowly squeezes his thumb and fingers together, pushing the inner tube assembly 50 in the outer tube assembly 40 until the specimen cage/bag assembly 15 is fully exposed, as best seen in FIG. 2.

The operator then removes said plug (not shown) in end cap 74 of the inner tube assembly 50 and inserts the grasping instrument 80 through the hole 75, through the center of the inner tube assembly 50 and the specimen cage/bag assembly 15, and grasps the specimen 30, as best seen in FIG. 2. The operator then pulls the specimen 30 into the cage/bag assembly 15, as far as possible, by retracting grasping laparoscopic instrument 80, as best seen in FIG. 3. After the specimen 30 is placed in the cage/bag assembly 15, the operator pulls the drawstrings 28 and 38 via ring 29 causing the end or tips of the specimen cage 20 or support means and, thus, liner 32 to be cinched closed, trapping the specimen 30 inside. After the specimen 30 has been placed in the cage/bag assembly 15, the grasping laparoscopic instrument 80 should be manipulated to release or deposit the specimen 30 in the cage/bag assembly 15 before fully retracting the grasping laparoscopic instrument 80.

The grasping instrument 80 can then be removed from the inner tube assembly 50 by fully retracting the grasping instrument 80 from the inner tube assembly 50 and an aspirator or morcelator may be inserted to remove tissue and fluids to further reduce the size of the specimen 30. The operator then extracts the laparoscopic specimen extractor 10 through the trocar or open site.

From the forgoing, it can be readily seen that an advantage of the laparoscopic specimen extractor 10 is its ability, through a single site, to (1) insert a grasping laparoscopic instrument 80 through (coaxially) the extractors' center; (2) retrieve a specimen 30 and pull the specimen 30 into the specimen cage/bag assembly 15 via the coaxially inserted grasping laparoscopic instrument 80; (3) compress the specimen cage/bag assembly 15 into an aerodynamic package; (4) aspirate and/or morcelate the specimen 30 in a protective environment; and, (5) remove the specimen 30 from the patient's cavity.

Referring now to the operation of the embodiment shown in FIGS. 6 and 7, in lieu of squeezing the thumb cradle 72 and finger rings 71 together to deploy the laparoscopic specimen extractor 10, the handle assembly 90 and finger rings 71' of the laparoscopic specimen extractor 10' are squeezed together. For example, the thumb may be placed over the end cap 74' and the fingers in the finger rings 71'. Thereafter, the operator slowly squeezes the thumb on the end cap 74' and the fingers in the finger rings 71' together.

The operation of the laparoscopic specimen extraction the laparoscopic specimen removal apparatus 100' (FIG. 10) and 100" (FIGS. 11–12) is essentially the same as that which has bee described above with respect to FIGS. 1–7.

Because many varying and differing embodiments may be made within the scope of the inventive concept herein taught and because many modifications may be made in the embodiment herein detailed in accordance with the descriptive requirement of the law, it is to be understood that the details herein are to be interpreted as illustrative and not in a limiting sense.

What is claimed as invention is:

1. A laparoscopic specimen extractor comprising:

(a) an outer tube assembly insertable in an incision or trocar;

(b) an inner tube assembly slidably mounted coaxially in said outer tube to slide between a retracted position to a deployed position and having an operator end and a patient end;

(c) a cage having one end securely coupled to said patient end and a free end wherein, when said inner tube assembly is in said retracted position, said cage is collapsed and contained in said outer tube assembly and, when said inner tube assembly is in said deployed position, said cage is at least partially ejected from said outer tube assembly and said free end automatically opened and expanded into a tulip shape, said cage comprising a plurality of spaced spring loaded strips secured to the inner circumferential wall of said patient end of said inner tube assembly and which project from said patient end wherein said free end of said cage comprises tips of said plurality of spaced spring loaded strips, each strip having a free end twisted approximately 90° (ninety degrees) with respect to the rest of itself to form a twisted section and a hole is bored in such twisted section wherein said twisted section is substantially perpendicular to a center axis of said inner tube assembly and said cage and wherein as the twisted sections are cinched closed, said cage forms a substantially elliptical or football shape;

(d) means journalled through said inner tube assembly and secured to said free end of said cage for cinching closed said free end; and, (e) a pathway coaxially through said inner tube assembly and said cage and adapted to have journalled therethrough said cinching close means, adapted to have inserted coaxially therethrough a grasping laparoscopic instrument for retrieving a specimen, adapted to have retracted therethrough said grasping laparoscopic instrument to deposit said specimen in said cage and adapted to aspirate or morcelate said specimen in said cage therethrough.

2. The extractor of claim 1, wherein said cage is lined with a liner or bag.

3. The extractor of claim 1, wherein said outer tube assembly includes a patient end and an operator end, and first and second finger rings oriented across from each other at said operator end of said outer tube assembly.

4. The extractor of claim 1, wherein said inner tube assembly comprises:

an end cap coupled to said operator end of said inner tube assembly;

a thumb cradle integrated with said end cap;

a center hole formed in said end cap to permit coaxial insertion of said laparoscopic instrument; and, an auxiliary hole formed in said end cap for passage of said cinching closed means journalled through said inner tube assembly.

5. The extractor of claim 4, wherein said cinching closed means comprises:

a first drawstring coupled to said tips of a first set of spring loaded strips of said plurality of spring loaded strips and journalled through said inner tube assembly;

a second drawstring coupled to said tips of a second set of spring loaded strips of said plurality of spring loaded strips and journalled through said inner tube assembly; and, means coupled to said first and second drawstrings for pulling said first and second drawstrings to cinch close, simultaneously, said tips of said first set of spring loaded strips and said tips of said second set of spring loaded strips.

6. The extractor of claim 5, wherein said pulling means comprises a ring.

7. The extractor of claim 5, wherein said inner tube assembly comprises:

an end cap coupled to said operator end of said inner tube assembly;

a center hole formed in said end cap to permit coaxial insertion of said laparoscopic instrument;

an auxiliary hole formed in said end cap for passage of said first and second drawstrings journalled through said inner tube assembly; and, wherein said pulling means comprises a drawstring handle assembly including:

a rod having one end secured to an outer wall of said end cap and projecting therefrom;

a palm rest integrated with a distal end of said rod; and, a finger squeeze slide slidably mounted on said rod and having secured thereto said first and second drawstrings wherein squeezing said palm rest and said finger squeeze slide slides said finger squeeze slide upward to said palm rest thus pulling said first and second drawstrings, simultaneously.

8. A laparoscopic specimen removal apparatus comprising:

(a) a grasping laparoscopic instrument for retrieving a specimen; and, (b) a laparoscopic specimen extractor comprising:

(i) an outer tube assembly insertable in an incision or trocar, (ii) an inner tube assembly slidably mounted coaxially in said outer tube to slide between a retracted position to a deployed position and having an operator end and a patient end, (iii) a cage having one end securely coupled to said patient end and a free end wherein, when said inner tube assembly is in said retracted position, said cage is collapsed and contained in said outer tube assembly and, when said inner tube assembly is in said deployed position, said cage is at least partially ejected from said outer tube assembly and said free end automatically opened and expanded into a tulip shape, said cage comprising a plurality of spaced spring loaded strips secured to the inner circumferential wall of said patient end of said inner tube assembly and which project from said patient end wherein said free end of said cage comprises tips of said plurality of spaced spring loaded strips, each strip having a free end twisted approximately 90° (ninety degrees) with respect to the rest of itself to form a twisted section and a hole is bored in such twisted section wherein said twisted section is substantially perpendicular to a center axis of said inner tube assembly and said cage;

(iv) means journalled through said inner tube assembly and secured to said free end of said cage for cinching closed said free end, and, (v) a pathway coaxially through said inner tube assembly and said cage and adapted to have inserted coaxially therethrough said grasping laparoscopic instrument for retrieving said specimen, adapted to have retracted therethrough said grasping laparoscopic instrument to deposit said specimen in said cage and adapted to aspirate or morcelate said specimen in said cage therethrough.

9. The apparatus of claim 8, wherein said cage is lined with a liner or bag.

10. The apparatus of claim 8, wherein said outer tube assembly includes a patient end and an operator end, and first and second finger rings oriented across from each other at said operator end of said outer tube assembly.

11. The apparatus of claim 8, wherein said inner tube assembly comprises:

an end cap coupled to said operator end of said inner tube assembly;

a thumb cradle integrated with said end cap;

a center hole formed in said end cap to permit coaxial insertion of said laparoscopic instrument; and, an auxiliary hole formed in said end cap for passage of said cinching closed means journalled through said inner tube assembly.

12. The apparatus of claim 11, wherein said cinching closed means comprises:

a first drawstring coupled to said tips of a first set of spring loaded strips of said plurality of spring loaded strips and journalled through said inner tube assembly;

a second drawstring coupled to said tips of a second set of spring loaded strips of said plurality of spring loaded strips and journalled through said inner tube assembly; and, means coupled to said first and second drawstrings for pulling said first and second drawstrings to cinch close, simultaneously, said tips of said first set of spring loaded strips and said tips of said second set of spring loaded strips.

13. The apparatus of claim 12, wherein said pulling means comprises a ring.

14. The apparatus of claim 12, wherein said inner tube assembly comprises:

an end cap coupled to said operator end of said inner tube assembly;

a center hole formed in said end cap to permit coaxial insertion of said laparoscopic instrument;

an auxiliary hole formed in said end cap for passage of said first and second drawstrings journalled through said inner tube assembly; and, wherein said pulling means comprises a drawstring handle assembly including:

a rod having one end secured to an outer wall of said end cap and projecting therefrom;

a palm rest integrated with a distal end of said rod; and, a finger squeeze slide slidably mounted on said rod and having secured thereto said first and second drawstrings wherein squeezing said palm rest and said finger squeeze slide slides said finger squeeze slide upward to said palm rest thus pulling said first and second drawstrings, simultaneously.

15. A laparoscopic specimen extractor comprising:

(a) a bag having open ends, (b) a means for supporting said bag comprising a plurality of spaced spring loaded strips secured to the inner circumferential wall said bag and which project from one end of said bag, said strips having a plurality of tips wherein said support means is spring biased and arranged to automatically open into a tulip shape when ejected to a deployed position, each of said strips having a free end twisted approximately 90° (ninety degrees) with respect to the rest of itself to form a twisted section and a hole is bored in such twisted section wherein said twisted section is substantially perpendicular to a center axis of said deployed bag;

(c) means coupled to said plurality of tips for cinching closed said support means, and (d) a pathway, formed coaxially through said laparoscopic specimen extractor and said support means and having said cinching closed means journalled axially therethrough wherein said pathway is adapted to have inserted coaxially therethrough a grasping laparoscopic instrument for retrieving said specimen, adapted to have retracted therethrough said grasping laparoscopic instrument to deposit said specimen in said bag and adapted to aspirate or morcelate said specimen in said bag therethrough.

16. The extractor apparatus of claim 15, wherein said support means cinches closed to a generally elliptical or football shape.

*17. A specimen extractor comprising:*

*(a) an outer assembly having an operator end and a patient end;*

*(b) an inner assembly having an operator end and a patient end, the inner assembly being slidably mounted with respect to the outer assembly and slidable between a retracted position and a deployed position;*

*(c) a cage coupled to the patient end of the inner assembly and having open and closed states, the cage comprising a base and a plurality of biased strips with tips which project from the patient end of the outer assembly when the inner assembly is placed in a deployed position;*

*(d) an actuator operatively connected to the cage, the actuator being able to change the state of the cage from open to closed by cinching closed the tips of the strips, wherein the actuator includes a first string connected to one or more of the tips and a second string attached to other of the tips; and*

*(e) wherein the cage is moved from open to closed when both the first and second strings are pulled, forming an elliptical shape.*

*18. The specimen extractor of claim 17, wherein the number of strips operatively connected to the plurality of strings is an even number and each string is connected to less than the total number of strips.*

*19. The specimen extractor of claim 17, wherein each string is operatively connected to at least two of the same tips of the strips.*

*20. A specimen extractor comprising:*

*(a) an outer assembly having an operator end and a patient end;*

*(b) an inner assembly having an operator end and a patient end, the inner assembly being slidably mounted with respect to the outer assembly and slidable between a retracted position and a deployed position;*

*(c) a cage coupled to the patient end of the inner assembly and having open and closed states, the cage comprising a base and a plurality of biased strips with tips which project from the patient end of the outer assembly when the inner assembly is placed in a deployed position; and*

*(d) an actuator operatively connected to the cage, the actuator being able to change the state of the cage from open to closed by cinching closed the tips of the strips, wherein when the cage is in an open state the cage has a tulip shape.*

*21. A specimen extractor comprising:*

*(a) an outer assembly having an operator end and a patient end;*

*(b) an inner assembly having an operator end and a patient end, the inner assembly being slidably mounted with respect to the outer assembly and slidable between a retracted position and a deployed position;*

*(c) a cage coupled to the patient end of the inner assembly and having open and closed states, the cage comprising a base and a plurality of biased strips with tips which project from the patient end of the outer assembly when the inner assembly is placed in a deployed position;*

*(d) an actuator operatively connected to the cage, the actuator being able to change the state of the cage from open to closed by cinching closed the tips of the strips, wherein when the cage is in a closed state and contains a specimen to be extracted the cage forms a substantially elliptical or football shape; and*

*(e) the actuator comprising a plurality of drawstrings, wherein a first drawstring cinches closed a first plurality of said tips and a second drawstring cinches closed a second plurality of said tips.*

*22. A specimen extractor comprising:*

*(a) an outer assembly having an operator end and a patient end;*

*(b) an inner assembly having an operator end and a patient end, the inner assembly being slidably mounted with respect to the outer assembly and slidable between a retracted position and a deployed position;*

*(c) a cage coupled to the patient end of the inner assembly and having open and closed states, the cage comprising a base and a plurality of biased strips with tips which project from the patient end of the outer assembly when the inner assembly is placed in a deployed position;*

*(d) an actuator operatively connected to the cage, the actuator being able to change the state of the cage from open to closed, generally elliptical shape by cinching closed the tips of the strips, wherein the cage has a liner; and*

*(e) the actuator comprising a plurality of drawstrings, wherein a first drawstring cinches closed a first plurality of said tips and a second drawstring cinches closed a second plurality of said tips.*

*23. A specimen extractor comprising:*

*(a) an outer assembly having a first end and a second end;*

*(b) an inner assembly having a first end and a second end, the inner assembly being slidably mounted with respect*

*to the outer assembly and slidable between a retracted position and a deployed position;*

(*c*) *a cage coupled to the second end of the inner assembly, the cage comprising a base, a front end, and a plurality of biased strips, the front end including an opening, and the cage having three states including a closed state when the inner assembly is in a retracted position, an open state when inner assembly is in a deployed position, and a cinched closed state when the inner assembly is in a deployed position and the cage is cinched closed, wherein the opening of the front end increases in size from cinched close, to closed, and then to open states;*

(*d*) *an actuator operatively connected to the cage, the actuator being able to change the state of the cage from the open state to the cinched closed state; and*

(*e*) *the actuator including multiple drawstrings that engage the plurality of biased strips, one drawstring engaging at least a first of said strips and a second drawstring that engages at least a second of said strips.*

*24. The specimen extractor of claim 23, wherein the plurality of strips have a plurality of tips, and wherein the actuator includes a plurality of strings operatively connected to the plurality of tips of the strips.*

*25. The specimen extractor of claim 24, wherein the number of strips operatively connected to the plurality of strings is an even number and each string is connected to less than the total number of strips.*

*26. The specimen extractor of claim 24, wherein each string is operatively connected to at least two of the same tips of the strips.*

*27. The specimen extractor of claim 23, wherein when the cage is in an open state the cage has a tulip shape.*

*28. The specimen extractor of claim 23, wherein when the cage is in a cinched closed state and contains a specimen to be extracted the cage forms a substantially elliptical or football shape.*

*29. The specimen extractor of claim 23, wherein the cage has a liner.*

*30. A specimen extractor comprising:*

(*a*) *an outer assembly having a proximal operator end, a distal patient end and an open ended bore;*

(*b*) *an inner assembly having a proximal operator end and a distal patient end, the inner assembly being slidably mounted in the bore of the outer assembly and being slidable relative to the outer assembly;*

(*c*) *a cage coupled to the patient end of the inner assembly, the cage comprising a base and a plurality of biased strips with tips that project distally from the patient end of the inner assembly;*

(*d*) *an actuator that moves the cage, wherein the actuator includes a plurality of strings that are connected to the plurality of tips of the strips, wherein one string attaches to at least a first one of the tips and a second string attaches to at least a second one of the strips;*

(*e*) *wherein the cage can be moved into a collapsed position by pulling the cage into the bore of the outer assembly, moving the inner assembly and cage relative to the outer assembly proximally;*

(*f*) *wherein the cage can be moved to a deployed position that enables intake of a specimen to be extracted by moving the inner assembly and cage distally until the cage is positioned distally of the patient end of the outer assembly; and*

(*g*) *wherein in the deployed position, the cage is biased to open distally and can be closed to an elliptical shape after intake of a specimen by pulling the multiple strings proximally.*

*31. The specimen extractor of claim 30, wherein the number of strips operatively connected to the plurality of strings is an even number and each string is connected to less than the total number of strips.*

*32. The specimen extractor of claim 30, wherein each string is operatively connected to at least two of the same tips of the strips.*

*33. A specimen extractor comprising:*

(*a*) *an outer assembly having a proximal operator end, a distal patient end, and an outer assembly bore;*

(*b*) *an inner assembly having a proximal operator end and a distal patient end, the inner assembly being slidably mounted in the outer assembly bore and with respect to the outer assembly;*

(*c*) *a cage coupled to the patient end of the inner assembly, the cage having collapsed, open and closed states, the cage comprising a base and a plurality of biased strips with tips which project distally from the patient end of the inner assembly;*

(*d*) *the cage being movable between collapsed and open positions by moving the inner assembly and cage from a position within the outer assembly bore to a position that spaces the cage distally of the outer assembly bore;*

(*e*) *an actuator operatively connected to the cage and including multiple circumferentially spaced drawstrings, each drawstring being connected to a different plurality of the tips, the actuator enabling a change of the state of the cage from open to closed by cinching closed the tips of the strips when the cage is positioned distally of the outer assembly bore;*

(*f*) *wherein when the cage is in an open position, the cage has a tapered shape that gradually increases in diameter distally, enabling intake in a distal to proximal direction of a specimen to be extracted; and*

(*g*) *a grasping instrument that has operator and patient ends, that grasping instrument being extendable through the inner assembly and cage, the patient end of the grasping instrument having a tool for enabling extraction of a specimen.*

* * * * *